(12) United States Patent
Tsuzuki et al.

(10) Patent No.: US 6,320,008 B2
(45) Date of Patent: Nov. 20, 2001

(54) POLYMERIC COLORANT AND COLORED MATERIAL FOR OCULAR LENS USING THE COLORANT

(75) Inventors: Akira Tsuzuki; Kazuharu Niwa, both of Nagoya; Tatsuya Ojio, Kasugai, all of (JP)

(73) Assignee: Menicon Co., Ltd., Nagoya (JP)

(*) Notice: Subject to any disclaimer, the term of this patent is extended or adjusted under 35 U.S.C. 154(b) by 0 days.

(21) Appl. No.: 09/836,906

(22) Filed: Apr. 17, 2001

Related U.S. Application Data (62) Division of application No. 09/251,377, filed on Feb. 17, 1999, now Pat. No. 6,242,551.

(51) Int. Cl.[7] .................................................. C08F 126/00

(52) U.S. Cl. .......................... 526/312; 526/310; 526/332

(58) Field of Search .................................. 526/310, 312, 526/332

(56) References Cited

U.S. PATENT DOCUMENTS

| 5,359,439 | 10/1994 | Miller et al. | 359/76 |
|---|---|---|---|
| 5,470,932 | 11/1995 | Jinkerson | 526/312 |

FOREIGN PATENT DOCUMENTS

| 1-280464 | 11/1989 | (JP) . |
|---|---|---|
| 1-299560 | 12/1989 | (JP) . |
| 8-503997 | 4/1996 | (JP) . |

*Primary Examiner*—Helen L. Pezzuto
(74) *Attorney, Agent, or Firm*—Burr & Brown

(57) ABSTRACT

A polymeric colorant represented by the following formula:

$$A_1\text{—N=N—}A_2\text{—O—}(CH_2)n\text{-X}$$

wherein, $A_1$ represents an aryl group which may have a substituent group, $A_2$ represents an arylene group which may have a substituent group, X represents one of an acryloyloxy group, a methacryloyloxy group, a vinylphenyl group, a vinylphenyloxy group, and a vinylphenylalkyloxy group whose alkyl portion has 1–5 carbon atoms, and n is an integer of 1–5, and a colored material for an ocular lens which uses to the polymeric colorant is also disclosed.

2 Claims, 5 Drawing Sheets

POLYMERIC COLORANT AND COLORED MATERIAL FOR OCULAR LENS USING THE COLORANT

This application is a divisional of Ser. No. 09/251,377, filed Feb. 17, 1999, now U.S. Pat. No. 6,242,551.

The present application is based on Japanese Patent Application No. 9-58807 filed Mar. 13, 1997, the content of which is incorporated hereinto by reference.

BACKGROUND OF THE INVENTION

1. Field of the Invention

The present invention relates to a polymeric colorant suitably used for coloring ocular lenses such as a contact lens, an intraocular lens and an artificial cornea, and a colored material for forming the ocular lenses, which uses the polymeric colorant.

2. Discussion of the Related Art

There have been proposed various polymeric colorants for coloring a composition or material which is used for forming a colored product. In the field of manufacture of an ocular lens such as a contact lens or an intraocular lens, for instance, a lens composition or material (lens-forming composition) used for producing the ocular lens is copolymerized with a suitable polymeric colorant, to thereby provide a colored material from which the intended ocular lens is produced. The ocular lens formed of such a colored material is uniformly colored and exhibits a high degree of resistance to exposure to light and chemical substances without suffering from decoloring or a change in its color, which would be caused by separation or elution of the colorant from the colored material.

JP-A-1-280464 discloses, as one example of the polymeric colorant for coloring the ocular lens, a polymeric colorant of azo-system or an azo-derived polymeric colorant wherein one of acryloyloxy, methacryloyloxy, vinyl, and aryl groups is substituted for at least one hydrogen atom of a naphthyl group which is bonded to an azo group. This polymeric colorant of the azo system is copolymerized with a vinyl monomer, to thereby provide a vinyl polymer from which the intended colored lens is produced.

JP-A-1-299560 discloses a colored ocular lens material obtained by copolymerizing a suitably selected copolymerizable lens-forming monomer component, a polymeric UV absorbent including a suitable polymeric group, and a polymeric colorant including a polymeric group which is selected from the group consisting of an acryloyl group, a methacryloyl group, a vinyl group, an aryl group, and an isopropenyl group. This colored ocular lens material does not suffer from elution of the UV absorbent and the colorant, and exhibits excellent durability. The colorant used in this ocular lens material is a polymeric colorant of azo system, wherein the polymeric group suitably selected from among those described above is introduced into a phenyl group or a naphthyl group bonded to the azo group, via an ester bond or an amide bond.

JP-A-8-503997 discloses a polymerizable yellow dye of azo system, wherein an unsaturated organic group having an ester structure or an amide structure is introduced into a phenyl group bonded to the azo group, via nitrogen or alkyl. This polymerizable yellow dye is polymerized with a lens-forming monomer component such as acrylate monomer or methacrylate monomer, to thereby provide a colored ocular lens material.

In those polymeric colorants described above wherein the polymeric unsaturated group is introduced via an oxygen atom into the aromatic ring in the phenyl or naphthyl group bonded to the azo group, the unsaturated group is bonded or attached to the aromatic ring by the ester bond formed therebetween. The polymeric colorant in which the ester bond is directly attached to the aromatic ring as described above tends to suffer from easy hydrolysis, whereby the colorant is chemically unstable, making its handling difficult. Further, the original color tone of the colorant undesirably changes due to the introduction of the polymeric group. In this case, it is difficult to predict the color tone of the colorant in the end product.

SUMMARY OF THE INVENTION

It is therefore a first object of the present invention to provide a novel polymeric colorant which is less likely to suffer from separation or elution, and is chemically stable without suffering from denaturation as caused by hydrolysis, while maintaining the original color tone, in spite of introduction of a suitably selected polymeric group therein.

It is a second object of the present invention to provide a colored ocular lens material having excellent characteristics, by using such a polymeric colorant.

The above-indicated first object of the invention may be attained according to a first aspect of the invention, which provides a polymeric colorant represented by the following formula:

wherein, $A_1$ represents an aryl group which may have a substituent group, $A_2$ represents an arylene group which may have a substituent group, X represents one of an acryloyloxy group, a methacryloyloxy group, a vinylphenyl group, a vinylphenyloxy group, and a vinylphenylalkyloxy group whose alkyl portion has 1–5 carbon atoms, and n is an integer of 1–5.

In the polymeric colorant obtained according to the above first aspect of the present invention, the colorant per se includes a suitable polymeric group (X). This colorant is chemically bonded to a composition or material for an intended product, to thereby provide a suitable colored material for forming the intended colored product. The colored material obtained by using the present polymeric colorant is free from discoloration which would arise from the elution of the colorant, even when the colored material is boiled or immersed in water or organic solvents. In the present polymeric colorant, the suitable polymeric group (X) is introduced into the aromatic ring ($A_2$) which bonds to the azo group, via the "—O—$(CH_2)_n$—" group, unlike the conventional colorants wherein the polymeric group is introduced via the ester bond. Accordingly, the present polymeric colorant is chemically stable without suffering from denaturation as caused by hydrolysis, assuring easy handling thereof. The colored material obtained by using the present polymeric colorant is capable of maintaining its color with high stability.

In the present polymeric colorant wherein the suitable polymeric group (X) is introduced into the aromatic ring ($A_2$) via the "—O—$(CH_2)n$—" group, the original color tone which derives from the colorant moiety is not changed by the introduced polymeric group. Accordingly, the polymeric colorant in the end product can maintain the original color with high stability. In addition, the polymeric group which is introduced into the aromatic ring ($A_2$) can be suitably and freely selected from among various polymeric groups.

In a first preferred form of the above first aspect of the present invention, the aryl group is one of a phenyl group, a naphthyl group, a substituted phenyl group, and a substituted naphthyl group.

In a second preferred form of the above first aspect of the present invention, the arylene group is a phenylene group which has at least one substituent group or a naphthylene group which has at least one substituent group. Preferably, the above-indicated at least one substituent group is selected from a group consisting of a hydroxyl group, a linear alkyl group having 1–6 carbon atoms, and a branched alkyl group having 1–6 carbon atoms.

The above-indicated second aspect of the present invention may be attained according to a second aspect of the present invention, which provides a colored material for an ocular lens, which is formed of a polymer obtained by copolymerizing at least one polymeric unsaturated monomer for the ocular lens and a polymeric colorant which is represented by the following formula:

$A_1\text{—}N\text{=}N\text{—}A_2\text{—}O\text{—}(CH_2)_n\text{-}X$ wherein, $A_1$ represents an aryl group which may have a substituent group, $A_2$ represents an arylene group which may have a substituent group, X represents one of an acryloyloxy group, a methacryloyloxy group, a vinylphenyl group, a vinylphenyloxy group, and a vinylphenylalkyloxy group whose alkyl portion has 1–5 carbon atoms, and n is an integer of 1–5.

In one preferred form of the above second aspect of the present invention, the polymeric colorant is used in an amount of 0.001–0.2 part by weight per 100 parts by weight of the above-indicated at least one unsaturated monomer for the ocular lens for copolymerization therewith.

BRIEF DESCRIPTION OF THE DRAWINGS

The above and optional objects, features, advantages and technical significance of the present invention will be better understood by reading the following detailed description of a presently preferred embodiment of the invention, when considered in conjunction of the accompanying drawings, in which.

DETAILED DESCRIPTION OF PREFERRED EMBODIMENT

In the present polymeric colorant represented by the above formula, $A_1$ is an aryl group which is a residue in the form of a monovalent substituent group, wherein one hydrogen atom is removed from the aromatic ring of the aromatic compound. In general, a phenyl group, a naphthyl group, a substituted phenyl group, or a substituted naphthyl group are used as the aryl group. A halogen atom such as chlorine, or a linear or a branched alkyl group having 1–6 carbon atoms such as methyl, ethyl or isopropyl may be substituted for the phenyl or naphthyl group.

In the present polymeric colorant represented by the above formula, $A_2$ is an arylene group which is a residue in the form of a divalent substituent group, wherein two hydrogen atoms are removed from the aromatic ring of the aromatic compound. In general, a phenylene or a naphthylene group which includes at least one substituent group is used as the arylene group. The substituent group introduced into the phenylene or naphthylene group may be a hydroxyl group, or a linear or a branched alkyl group having 1–6 carbon atoms such as a methyl group or a tert-butyl group.

Examples of the polymeric colorant which is represented by the above formula include 2-phenylazo-4-(meth)acryloyloxyethoxy-6-tert-butylphenol, 2-(4-methyl)phenylazo-4-(meth)acryloyloxyethoxy-6-tert-butylphenol, 2-(3-methyl)phenylazo-4-(meth)acryloyloxyethoxy-6-tert-butylphenol, 2-(4-chloro)phenylazo-4-(meth)acryloyloxyethoxy-6-tert-butylphenol, 2-(2-chloro)phenylazo-4-(meth)acryloyloxyethoxy-6-tert-butylphenol, 2-phenylazo-4-(meth)acryloyloxypropoxy-6-tert-butylphenol, 2-(4-methyl)phenylazo-4-(meth)acryloyloxypropoxy-6-tert-butylphenol, 2-(3-methyl)phenylazo-4-(meth)acryloyloxypropoxy-6-tert-butylphenol, 2-(4-chloro)phenylazo-4-(meth)acryloyloxypropoxy-6-tert-butylphenol, 2-(2-chloro)phenylazo-4-(meth)acryloyloxypropoxy-6-tert-butylphenol, 2-phenylazo-4-(meth)acryloyloxybutoxy-6-tert-butylphenol, 2-phenylazo-4-(meth)acryloyloxyethoxy-6-methylphenol, 2-phenylazo-4-(meth)acryloyloxyethoxy-6-(2-methyl)butylphenol, 2-(1-naphthylazo)-4-(meth)acryloyloxyethoxy-6-tert-butylphenol, 2-(4-methyl-1-naphthylazo)-4-(meth)acryloyloxyethoxy-6-tert-butylphenol, 2-(4-chloro-1-naphthylazo)-4-(meth)acryloyloxyethoxy-6-tert-butylphenol, 2-(1-naphthylazo)-4-(meth)acryloyloxypropoxy-6-tert-butylphenol, 2-(1-naphthylazo)-4-(meth)acryloyloxyethoxy-6-methylphenol, 2-phenylazo-4-(4-vinyl)phenoxyethoxy-6-tert-butylphenol, 1-phenylazo-4-(meth)acryloyloxyethoxy-2-naphthol, 2-phenylazo-4-(4-vinyl)benzyloxy-6-tert-butylphenol, and 2-phenylazo-4-(4-vinyl)benzyl-6-tert-butylphenol. In the above compounds," . . . (meth)acryloyloxy . . . " is generic to the following two compounds: " . . . acryloyloxy . . . " and " . . . methacryloyloxy . . . ".

The polymeric colorant described above can be easily produced by utilizing known reactions. For instance, the polymeric colorant represented by the above formula where X in the formula is one of acryloyloxy, methacryloyloxy, vinylphenyloxy, and vinylphenylalkyloxy groups, is obtained in the following manner. Initially, a phenol or a naphthol derivative (whose typical example is tert-butylhydroquinone) is hydroxyalkylated at its end by a hydroxyalkylation agent Such as ethylenechlorohydrin, in water or a suitable organic solvent, to thereby provide a synthetic intermediate product A. In the meantime, an aromatic amine whose typical example is aniline is subjected to diazotization by using sodium nitrite, to thereby provide a diazonium salt. The obtained diazonium salt is coupled to the intermediate product A prepared as described above in the presence of alkali, so that a synthetic intermediate product B is obtained. This intermediate product B is subjected to a condensation reaction with (meth)acrylic chloride, or halogenated alkylstyrene (whose typical example is chloromethylstyrene), in the presence of metallic magnesium or an organic base such as triethylamine or 1,8-diazabicyclo[5,4,0]undecene-7 (DBU), in an organic solvent such as dehydrated methylene chloride, which solvent does not include a functional group such as a hydroxyl group or an amino group. Thus, the intended polymeric colorant is obtained.

The polymeric colorant which is represented by the above formula where X in the formula is a vinylphenyl group or a vinylphenylalkyl residue, is obtained in the following manner. Initially, the aromatic amine whose typical example is aniline is subjected to the diazotization by using sodium nitrite, to thereby provide the diazonium salt. The obtained diazonium salt is coupled to the phenol or naphthol derivative (whose typical example is tert-butylhydroquinone), in the presence of alkali, so that a synthetic intermediate product C is obtained. This intermediate product C is subjected to the condensation reaction with the halogenated alkylstyrene (whose typical example is chloromethylstyrene), in the presence of metallic magnesium or an organic base such as DBU, in an organic solvent such as dehydrated methylene chloride, which solvent does not include a polyfunctional group such as a hydroxyl or an amino group. Thus, the intended polymeric colorant is obtained.

In producing the intended colored material for the ocular lens by using the polymeric colorant prepared as described above, the polymeric colorant is added to and mixed with a suitable polymeric lens-forming composition. Then, the mixture is copolymerized to provide the colored material for the ocular lens. The lens-forming composition to be copolymerized with the polymeric colorant is suitably selected from among known monomers having at least one polymeric unsaturated bond. Examples of the monomer include: (meth) acrylates such as alkyl (meth)acrylate, siloxanyl (meth) acrylate, fluoroaklyl (meth)acrylate, hydroxyalkyl (meth) acrylate, phenoxyalkyl (meth)acrylate, phenylalkyl (meth) acrylate, polyethyleneglycol (meth)acrylate and polyhydric alcohol (meth)acrylate; derivatives of styrene; and N-vinyllactam. As needed, a polyfunctional monomer such as ethyleneglycol di(meth)acrylate or diethyleneglycol di(meth)acrylate is added as a cross-linking agent. Other examples of the monomer are described in detail in laid-open publication JP-A-1-280464 of Japanese Patent Application which was filed by the assignee of the present invention. In the present invention, the monomers disclosed in the publication and other monomers known in the art are suitably used.

In producing the intended colored ocular lens material by copolymerizing the above-indicated lens-forming composition and the polymeric colorant, the polymeric colorant is used in an amount of 0.001–0.2 part by weight per 100 parts by weight of the lens-forming composition. If the amount of the polymeric colorant is smaller than the lower limit of 0.001 part by weight, the lens material to be obtained is not sufficiently colored. On the other hand, if the amount of the polymeric colorant exceeds the upper limit of 0.2 part by weight, the obtained lens material is excessively colored (having an excessively high color tone), giving rise to problems in practical use. For instance, the excessively colored lens material does not permit sufficient transmission of the visible rays therethrough.

The mixture of the polymeric colorant and the lens-forming composition is polymerized according to any known methods. For instance, the mixture to which a radical polymerization initiator has been added as needed is gradually heated from the room temperature to about 130° C., so that the mixture is polymerized to provide the intended colored ocular lens material. Alternatively, the mixture is polymerized by exposure to an electromagnetic radiation such as microwave, ultraviolet radiation, or γ ray. The polymerization of the mixture may be effected according to a bulk polymerization method or a solution polymerization method using a solvent. The mixture may be heat-polymerized with its temperature raised in steps. Other known polymerization methods may be suitably employed in the present invention.

As the radical polymerization initiator, azobisisobutyronitrile, azobisdimethylvaleronitrile, benzoylperoxide, tert-butylhydroperoxide, and cumenehydroperoxide may be used, for instance. At least one suitably selected radical polymerization initiator is added to the mixture of the polymeric colorant and the lens-forming composition. The radical polymerization initiator is included in the mixture generally in an amount of 0.01–1 part by weight per 100 parts by weight of the mixture.

The ocular lens such as the contact lens or intraocular lens may be produced according to any methods known in the art. For instance, the mixture of the polymeric colorant and the lens-forming composition is polymerized in a suitable mold or container, to thereby provide a bar-shaped, block-shaped, or plate-shaped blank (polymer). The obtained polymer blank is subjected to machining operations such as cutting and grinding, whereby the ocular lens having a desired configuration is produced. Alternatively, the mixture is polymerized in a mold whose profile follows that of the intended ocular lens. The obtained polymerized product is subjected to machining operations, as needed, so as to provide the intended ocular lens. In producing the intraocular lens which is to be inserted within the eye, a support member(s) of the intraocular lens, which holds the lens body in position within the eye, may be prepared separately from the lens body to be obtained from the polymerized product, and later fixed to the lens body. Alternatively, the support member(s) may be formed integrally with the lens body upon polymerization of the mixture in a mold cavity.

To further clarify the concept of the present invention, some examples of the invention will be described. It is to be understood that the invention is not limited to the details of the illustrated example, but may be embodied with various changes, modifications and improvements, which may occur to those skilled in the art without departing from the scope of the invention defined in the attached claims.

EXAMPLES

Example 1

<Preparation of 2-phenylazo-4-(2-hydroxy)ethoxy-6-tert-butylphenol>

Figure 1:
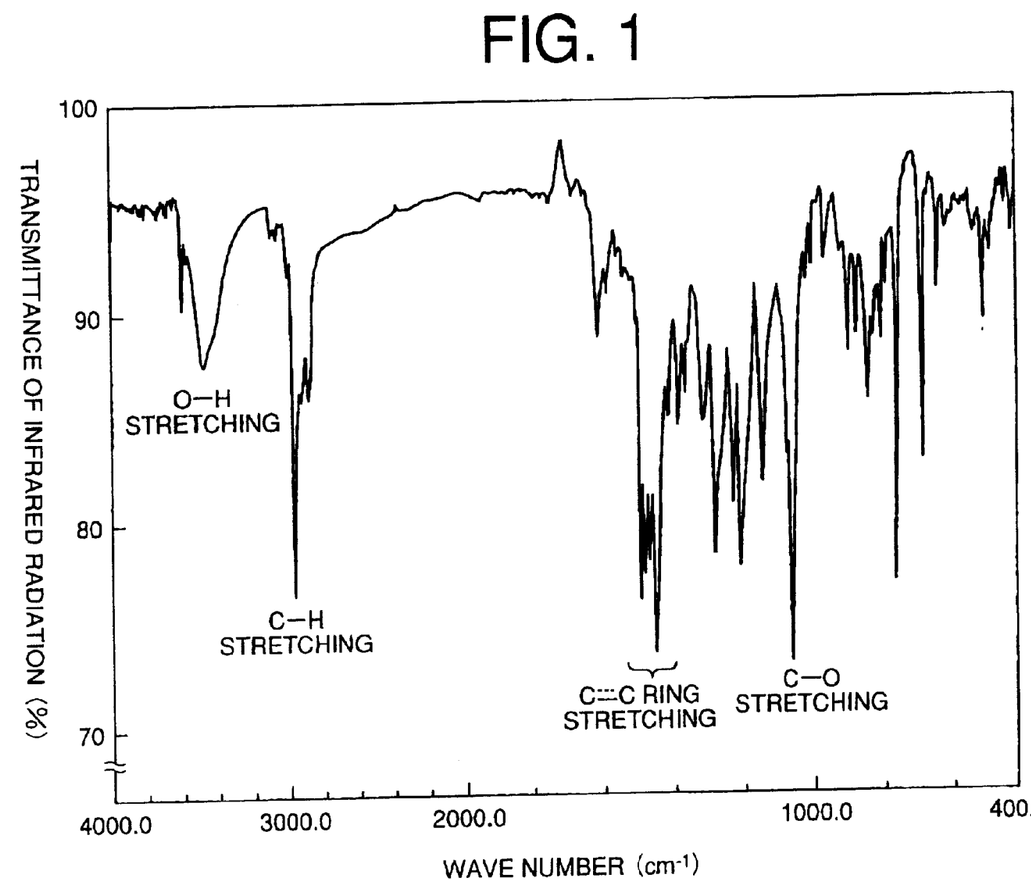
FIG. 1 is a graph showing an infrared radiation absorption spectrum of 2-phenylazo-4-(2-hydroxy)ethoxy-6-tert-butylphenol, which spectrum was obtained by IR analysis.

Initially, the diazotization of 9.30 g (0.10 mol) of aniline was effected in a known manner. Next, into a four-neck flask whose capacity is one liter and which is equipped with a stirrer, a dropping funnel, a thermometer and a cock, there were introduced 100 ml of ethanol, 21.04 g (0.10 mol) of 4-(2'-hydroxy)ethoxy-2-tert-butylphenol, and 100 ml of 10% aqueous solution of sodium hydroxide. The diazotized aniline was added dropwise for 30 minutes into the reaction solution in the flask prepared as described above. After the dropping was completed, the reaction mixture was stirred for 30 minutes. Then, the reaction mixture was filtered to collect a solid substance. After this solid substance was dissolved in methylene chloride, it was washed with water three times. Subsequently, the solvent was removed from the substance, to thereby provide crude crystal. Then, the obtained crude crystal was recrystallized with methanol, whereby 15.90 g of reddish needle crystal was obtained. This needle crystal was subjected to an IR analysis by using "FT/IR-8300" available from JAPAN SPECTROSCOPIC CO., LTD., Japan. The IR analysis revealed that the crystal was the intended substance, i.e., 2-phenylazo-4-(2hydroxy) ethoxy-6-tert-butylphenol. The infrared radiation absorption spectrum of this substance obtained by the IR analysis is shown in the graph of FIG. 1.

Example 2

<Preparation of 2-phenylazo-4-methacryloyloxyethoxy-6-tert-butylphenol>

Into a 500 ml-three-neck flask equipped with a stirrer, a dropping funnel with a calcium chloride-filled tube, and a thermometer, there were introduced 300 ml of methylene chloride, 6.28 g of 2-phenylazo-4-(2-hydroxy)ethoxy-6-tert-butylphenol prepared in the above Example 1, and 2.02 g (0.02 mol) of triethylamine. 2.30 g (0.022 mol) of chloride methacrylate which had been diluted with 15 ml of methylene chloride was added dropwise for 30 minutes into the reaction solution in the flask prepared as described above at a temperature of not higher than 3° C. After the reaction mixture was stirred overnight, it was washed with water three times, and the solvent was removed from the reaction mixture at a reduced pressure, whereby a reddish solid substance was obtained. 7.37 g of the obtained reddish solid substance was isolated by column chromatography. From the second fraction developed by methylene chloride, 5.60 g of crude crystal of 2-phenylazo-4-methacryloyloxyethoxy-6-tert-butylphenol was obtained.

Figure 2:
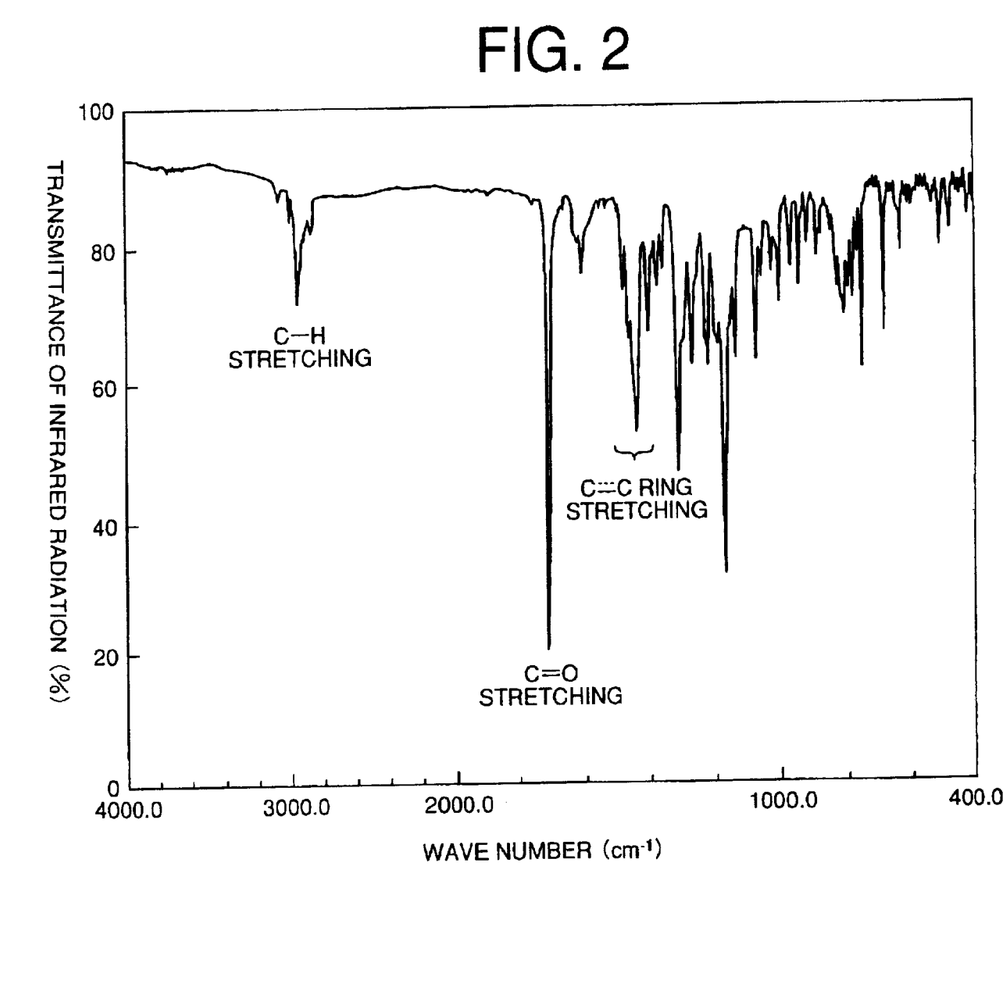
FIG. 2 is a graph showing an infrared radiation absorption spectrum of 2-phenylazo-4-methacryloyloxyethoxy-6-tert-butylphenol as the polymeric colorant obtained by IR analysis according to the present invention.

Subsequently, the thus obtained crude crystal was recrystallized with methanol, so that 4.04 g of a reddish needle crystal was obtained. This needle crystal was subjected to the IR analysis by using "FT/IR-8300" available from JAPAN SPECTROSCOPIC CO., LTD., Japan, and an NMR analysis by using "Gemi 2000/400BB" at 400 MHz, available from Varian, U.S.A. The analyses revealed that the needle crystal was the intended substance, i.e., 2-phenylazo-4-methacryloyloxyethoxy-6-tert-butylphenol. The infrared absorption spectrum of the substance obtained by the IR analysis is shown in the graph of FIG. 2, while the result of the NMR analysis ($^1$H-nuclear magnetic resonance spectrum) is as follows:

$^1$H-NMR(400 MHz, CDCl$_3$), δ1.45[9H, s, —C(CH$_3$)$_3$], δ1.97(3H, s, —CH$_3$), δ4.28(2H, t, —CH$_2$—), δ4.53(2H, t, —CH$_2$—), δ5.60(1H, s, =CH), δ6.17(1H, s, =CH), δ7.00~7.90(7H, m, benzene ring)

Example 3

<Preparation of the Colored Ocular Lens Material Specimen No. 1>

Figure 3:
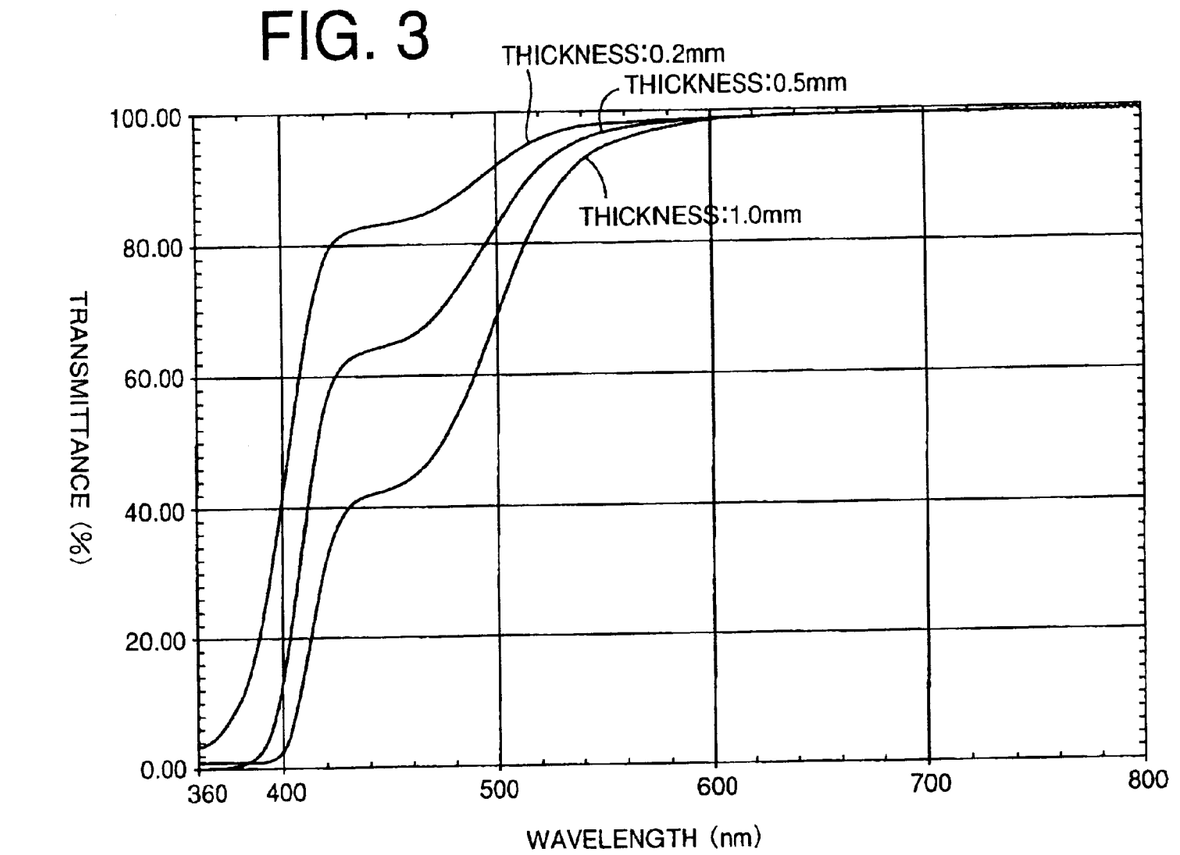
FIG. 3 is a graph showing light transmission spectra of the specimens No. 1 of the colored ocular lens material obtained in Example 3 and having different thickness values.

Initially, 0.02 part by weight of 2-phenylazo-4-methacryloyloxyethoxy-6-tert-butylphenol prepared in the above Example 2, 97 parts by weight of methyl methacrylate, 3 parts by weight of ethyleneglycol dimethacrylate, 0.18 part by weight of 2-[2'-hydroxy-5'-(2"-methacryloyloxyethoxy)-3'-tert-butylphenyl]-5-methyl-2H-benzotriazole, and 0.05 part by weight of azobisisobutyronitrile were mixed and dissolved together. The thus obtained mixture was introduced into a silicone-coated test tube made of a glass material. The test tube was heated from 35° C. to 130° C., with the opening of the test tube being plugged. Thus, the mixture in the test tube was polymerized into a polymer by a bulk polymerization method. The thus obtained polymer was subjected to a cutting operation and a surface grinding operation, to thereby provide three plates with different thickness values of 0.2 mm, 0.5 mm, and 1.0 mm, respectively. For each of the plates, the spectral transmittance at 360–800 nm was measured by using an auto-recording spectrophotometer ("UV-3100" available from SHIMAZU SEISAKUSHO, CO., LTD., Japan). The result of the measurement is shown in the graph of FIG. 3, The appearance of each of the three plates was visually inspected. The visual inspection revealed that all of the three plates were reddish yellow.

Example 4

<Preparation of the Colored Ocular Lens Material Specimen No.2>

Initially, 0.013 part by weight of 2-phenylazo-4-methacryloyloxyethoxy-6-tert-butylphenol prepared in the above Example 2, and 100 parts by weight of 2-hydroxyethylmethacrylate, 0.2 part by weight of ethyleneglycol dimethacrylate, 0.25 part by weight of 2-[2'-hydroxy-5'-(2"-methacryloyloxyethoxy-3'-tert-butylphenyl]-5-methyl-2H-benzotriazole, and 0.1 part by weight of 2,2'-azobis(2,4-dimethylvaleronitrile) were mixed and dissolved together. The thus obtained mixture was introduced into a silicone-coated test tube made of a glass material. The test tube was heated from 35° C. to 80° C., with the opening of the test tube being plugged. Thus, the mixture in the test tube was polymerized into a polymer by a bulk polymerization method. The thus obtained polymer was subjected to a cutting operation and a surface grinding operation, to thereby provide a plate having a thickness value of 0.5 mm. The appearance of the plate was reddish yellow.

Figure 4:
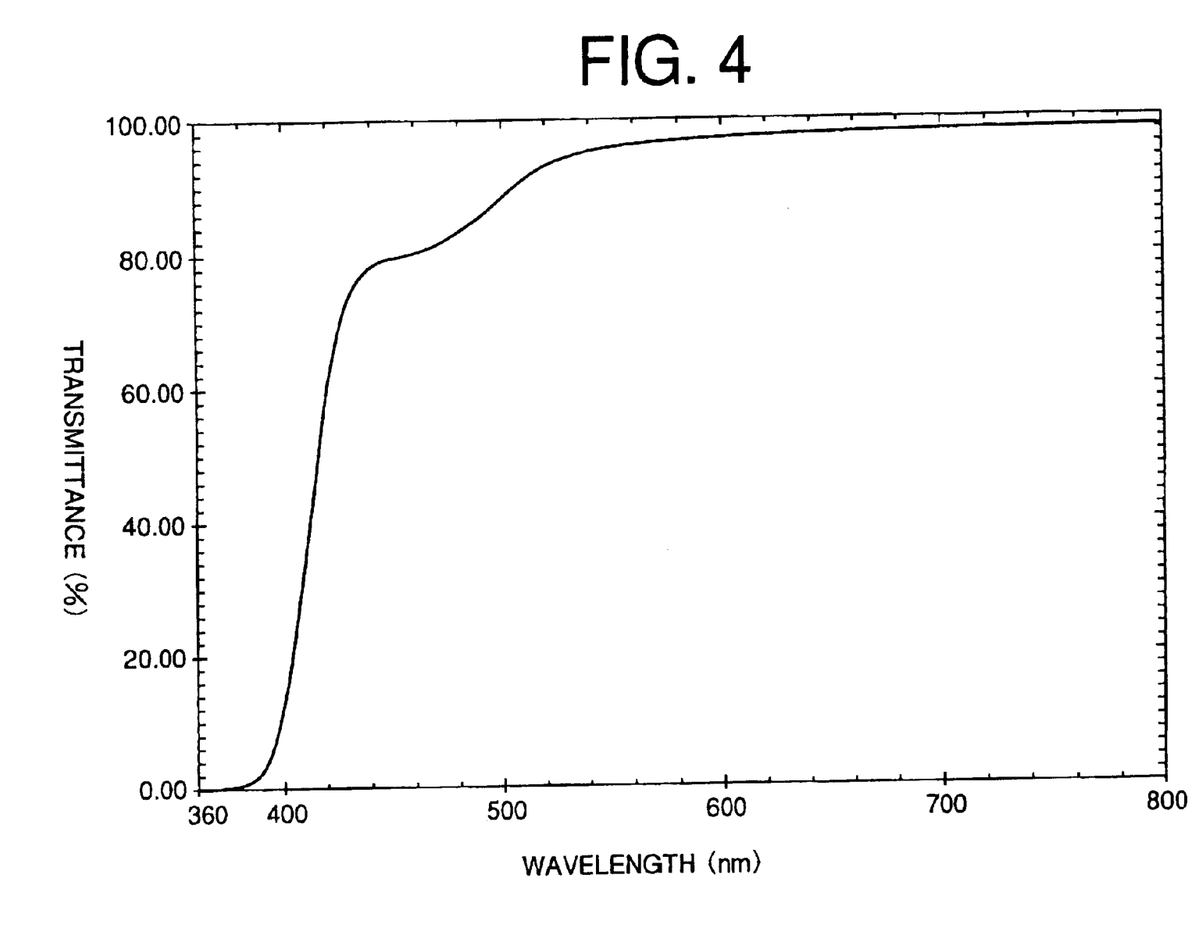
FIG. 4 is a graph showing a light transmission spectrum of the specimen No. 2 of the colored ocular lens material obtained in Example 4, which spectrum was obtained after the specimen was boiled for two hours.
Figure 5:
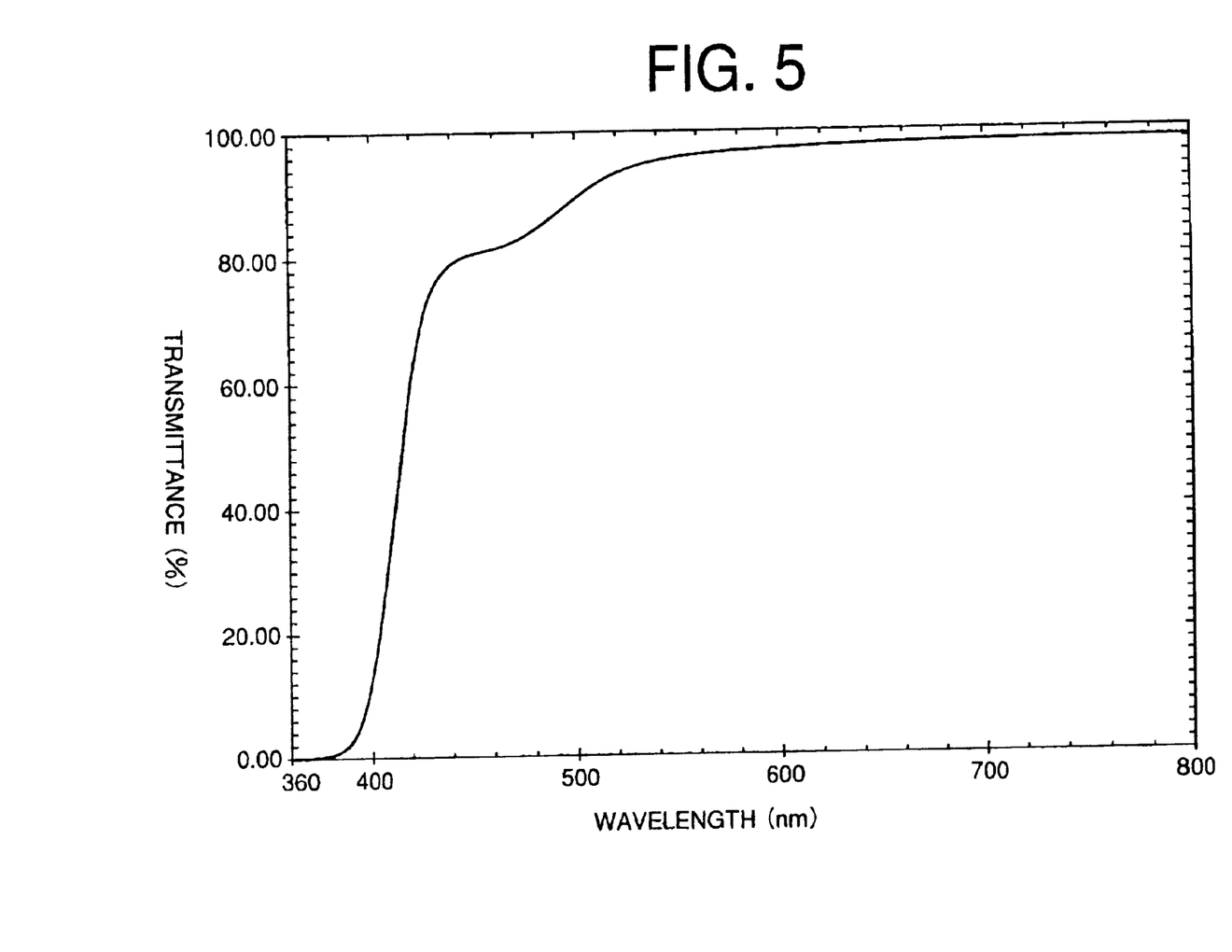
FIG. 5 is a graph showing a light transmission spectrum of the specimen used in FIG. 4, which spectrum was obtained after the specimen was further boiled for 48 hours.

Thereafter, the thus obtained plate was immersed in a physiological salt solution or saline for 16 hours, and boiled therein for two hours. The boiled plate was measured of its spectral transmittance at 360–800 nm in a manner similar to that in the above Example 3. The result is shown in the graph of FIG. 4. This plate was further boiled for 48 hours, and similarly measured of its spectral transmittance. The result is shown in the graph of FIG. 5. On the basis of the spectrum data after 2-hour boiling and after the additional 48-hour boiling, a chrominance, namely, a color difference between the two data was calculated according to a method as specified in JIS-Z-8730. The chrominance ΔE*ab was 0.51.

As is apparent from the explanation of the above Examples, the colored ocular lens materials which were obtained by including the polymeric colorant according to the present invention assume reddish yellow, and have a color tone suitable for practical use. It is to be understood from the results of the graphs of FIGS. 4 and 5 that the spectral transmittance of the ocular lens material (specimen No. 2) remains unchanged after the additional boiling operation. This indicates that the present polymeric colorant does not eluate or separate from the ocular lens material. Further, the polymeric colorant does not suffer from hydrolysis, and assures sufficiently high safety to the eye.

What is claimed is:

1. A colored material for an ocular lens which is formed of a polymer obtained by copolymerizing at least one polymeric unsaturated monomer for said ocular lens and a polymeric colorant which is represented by the following formula:

wherein, A$_1$ represents an aryl group which may have a substituent group, A$_2$ represents an arylene group which may have a substituent group, X represents one of an acryloyloxy group, a methacryloyloxy group, a vinylphenyl group, a vinylphenyloxy group, and a vinylphenylalkyloxy group whose alkyl portion has 1–5 carbon atoms, and n is an integer of 1-5.

2. A colored material according to claim 1, wherein said polymeric colorant is used in an amount of 0.001–0.2 parts by weight per 100 parts by weight of said at least one unsaturated monomer for said ocular lens for copolymerization therewith.

* * * * *